(12) United States Patent
Walavalkar et al.

(10) Patent No.: US 9,410,887 B2
(45) Date of Patent: Aug. 9, 2016

(54) OPTICAL SENSOR FOR ANALYTE DETECTION

(71) Applicant: California Institute of Technology, Pasadena, CA (US)

(72) Inventors: Sameer Sudhir Walavalkar, Studio City, CA (US); Andrew Peter Homyk, South Pasadena, CA (US); William Maxwell Jones, Pasadena, CA (US); Axel Scherer, Barnard, VT (US); Scott Fraser, Pasadena, CA (US); Thai Viet Truong, Pasadena, CA (US)

(*) Notice: Subject to any disclaimer, the term of this patent is extended or adjusted under 35 U.S.C. 154(b) by 118 days.

(21) Appl. No.: 14/046,739

(22) Filed: Oct. 4, 2013

(65) Prior Publication Data

US 2014/0099732 A1    Apr. 10, 2014

Related U.S. Application Data

(60) Provisional application No. 61/710,472, filed on Oct. 5, 2012.

(51) Int. Cl.
*G01N 21/63* (2006.01)
*G01N 21/64* (2006.01)

(52) U.S. Cl.
CPC ............ *G01N 21/63* (2013.01); *G01N 21/6428* (2013.01)

(58) Field of Classification Search
CPC ............................ G01N 21/63; G01N 21/6328
See application file for complete search history.

(56) References Cited

U.S. PATENT DOCUMENTS

| | | | |
|---|---|---|---|
| 2008/0050082 A1* | 2/2008 | Mitomi | G02F 1/0356 385/131 |
| 2008/0137063 A1 | 6/2008 | Naya | |
| 2009/0069193 A1 | 3/2009 | Flemming et al. | |
| 2009/0236614 A1 | 9/2009 | Puscasu et al. | |
| 2011/0116089 A1* | 5/2011 | Schmidt | G01N 21/658 356/301 |
| 2011/0128536 A1 | 6/2011 | Bond et al. | |
| 2011/0151605 A1 | 6/2011 | Yoon | |
| 2011/0267608 A1* | 11/2011 | Ou | G01N 21/658 356/301 |
| 2012/0088229 A1 | 4/2012 | Opitz et al. | |
| 2012/0162640 A1 | 6/2012 | Sakagami | |
| 2012/0322164 A1* | 12/2012 | Lal | B82Y 10/00 436/501 |
| 2014/0015548 A1* | 1/2014 | Naughton | G01R 27/26 324/658 |

FOREIGN PATENT DOCUMENTS

| | | |
|---|---|---|
| EP | 2 133 688 A1 | 12/2009 |
| EP | 2 264 438 A1 | 12/2010 |
| WO | WO 2014/055951 A1 | 4/2014 |

OTHER PUBLICATIONS

International Search Report and Written Opinion in corresponding PCT Application No. PCT/US2013/063581, mailed Jan. 17, 2014, 13 pages.
M. Mansuripur et al.: "Plasmonic Nano-structures for Optical Data Storage", SPIE, PO Box 10 Bellingham WA 98227-0010 USA, vol. 7505, 2009, XP040504263, DOI: 10.1117/12.838505.
Extended European Search Report mailed Jun. 22, 2016 in corresponding European Application No. 13844221.5, 8 pgs.

* cited by examiner

*Primary Examiner* — Melanie Y Brown
(74) *Attorney, Agent, or Firm* — Knobbe, Martens, Olson & Bear, LLP

(57) ABSTRACT

Devices, systems, and methods for detection of an analyte in a sample are disclosed. In some embodiments, an optical sensor can include a metallic layer and a plurality of dielectric pillars extending through the metallic layer. A plurality of regions of concentrated light can be supported in proximity to the ends of the plurality of dielectric pillars when a surface of the metallic layer is illuminated. Concentrated light within one or more of these regions can interact with an analyte molecule, allowing for detection of the analyte.

23 Claims, 17 Drawing Sheets

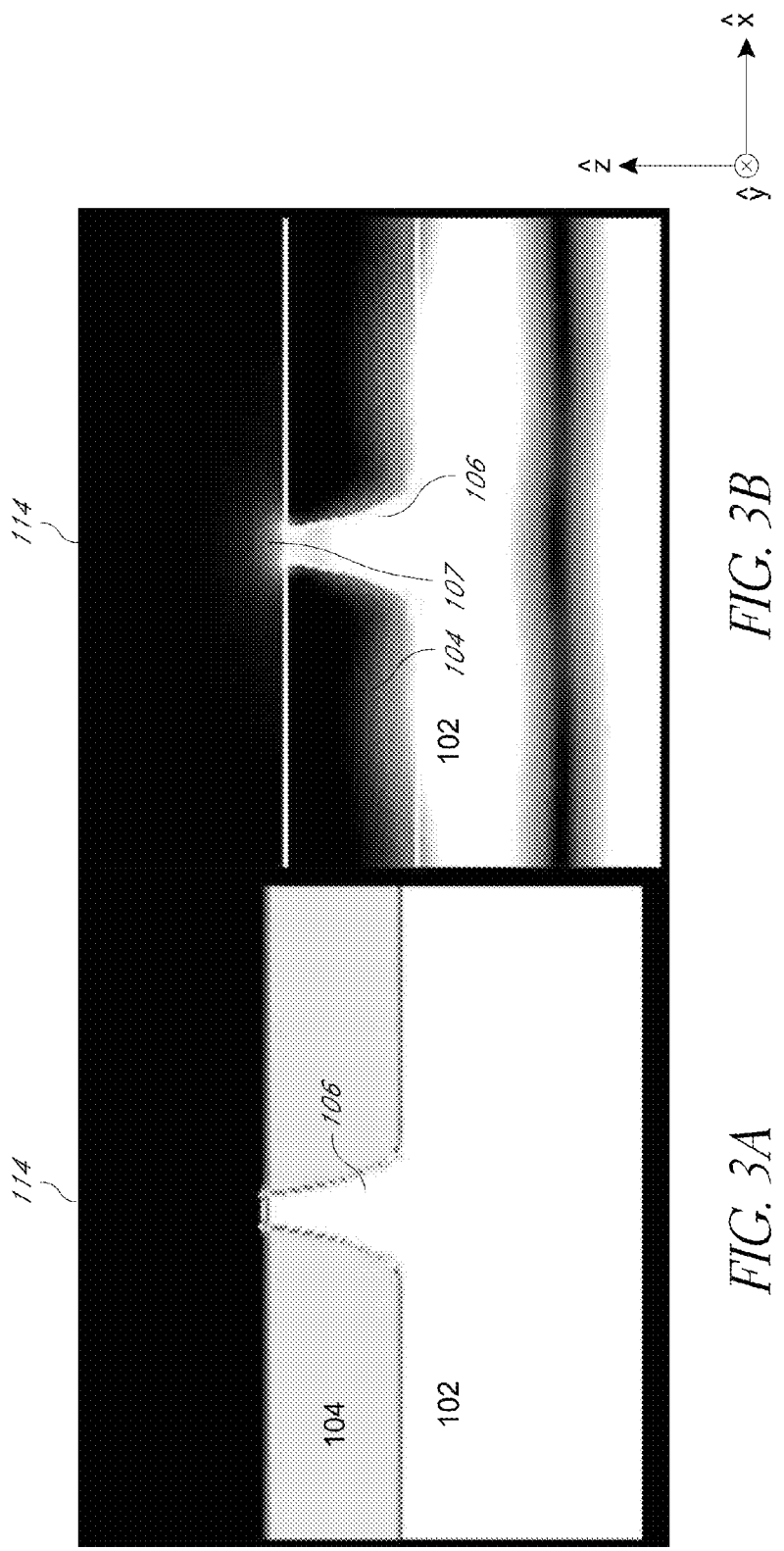

800

OPTICAL SENSOR FOR ANALYTE DETECTION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application claims a priority benefit under 35 U.S.C. §119(e) to U.S. Provisional Patent Application 61/710,472, filed on Oct. 5, 2012, and entitled "ETCHED, TEMPLATED PLASMONIC APERTURES FOR BIO-SENSING AND IMAGING," the entirety of which is hereby incorporated by reference.

BACKGROUND

1. Field

Various embodiments described herein relate to the field of optical sensors for detection of an analyte in a sample.

2. Description of the Related Art

There is a need in many industries, including medical, environmental, pharmaceutical, forensic, and many others, to be able to detect and characterize an analyte in a sample. For example, it can be desirable to qualitatively assess and/or quantitatively measure the presence, location, and/or amount of an analyte in the sample. The analyte of interest may be, for example, a molecule, such as a protein, DNA, etc.

A number of optical chemical and biological sensors have been developed for characterizing an analyte in a sample. Such sensors have taken advantage of many optical principles and techniques, including ellipsometry, spectroscopy, interferometry, and surface plasmon resonance. In some optical sensors a desired analyte quantity can be determined by measuring, for example, an optical characteristic of the analyte, or the effect of the analyte on an optical characteristic of the sensor, such as refractive index, resonance, absorbance, fluorescence, etc.

SUMMARY

In some embodiments, a device for detecting an analyte within a sample is disclosed, the device comprising: a metallic layer; and a plurality of dielectric pillars extending through the metallic layer, wherein a plurality of regions of concentrated light are supported in proximity to the ends of the plurality of dielectric pillars when a surface of the metallic layer is illuminated. The plurality of dielectric pillars may be nano-scale structures. The plurality of regions of concentrated light can comprise spatially-separated voxels above each of the plurality of dielectric pillars to which the light is substantially confined. The plurality of dielectric pillars can be functionalized such that they are capable of specifically binding to an analyte of interest. The analyte of interest can interact with the regions of concentrated light to create a signal for detecting the analyte.

The device can also comprise a dielectric layer having a top surface and a bottom surface, wherein the metallic layer is formed on the top surface of the dielectric layer, and wherein the plurality of regions of concentrated light are supported in proximity to the ends of the plurality of dielectric pillars when the bottom surface of the metallic layer is illuminated.

A window can be formed on the bottom surface of the dielectric layer below the plurality of dielectric pillars. A light source can be provided to illuminate the bottom surface of the dielectric layer or the metallic layer through the window. An optical detector can be provided to receive light from, for example, an object located in one of the regions of concentrated light.

In some embodiments, the dielectric layer and the dielectric pillars comprise silicon or silicon dioxide, and the metallic layer comprises gold or silver.

In some embodiments, an analyte detection method comprises: pumping an optical sensor with light, the optical sensor comprising a metallic layer, and a plurality of dielectric pillars extending through the metallic layer; and receiving light from the optical sensor to detect an analyte of interest in a sample located in proximity to the optical sensor. Pumping the optical sensor with light can cause a plurality of regions of concentrated light in proximity to the ends of the plurality of dielectric pillars to be supported. An analyte molecule can interact with a region of concentrated light to create a signal for detecting the analyte.

In some embodiments, the signal may comprise light emitted from a labeled analyte molecule. The labeled analyte molecule may be bound to one of the dielectric pillars. In some embodiments, the signal may comprise scattered light from a region of concentrated light by an analyte molecule that is bound to one of the dielectric pillars. The method may also comprise measuring the light from the optical sensor at a plurality of wavelengths and detecting the analyte based on a change in the spectrum caused by the presence of the analyte within at least one of the regions of concentrated light.

In some embodiments, the location of an analyte molecule can be detected with sub-diffraction-limited resolution. The method may comprise pumping the plurality of dielectric pillars using light having a first polarization angle; receiving light from the optical sensor to detect the analyte of interest while pumping the plurality of dielectric pillars using light having the first polarization angle; pumping the plurality of dielectric pillars using light having a different second polarization angle; receiving light from the optical sensor to detect the analyte of interest while pumping the plurality of dielectric pillars using light having the second polarization angle; and images of the light received from the optical sensor to determine the location of the analyte.

A method of fabricating an optical sensor may comprise: providing a substrate; etching a plurality of pillars into a top surface of the substrate; applying a metallic layer over the plurality of pillars and the substrate; and etching a window beneath the plurality of pillars into the bottom surface of the substrate. The method may also comprise removing metal from the sidewalls of the plurality of pillars by heating the metallic layer, thus causing it to reflow. The method may also comprise applying mechanical force to break off at least a portion of the plurality of dielectric pillars that extend above the top surface of the metallic layer.

Specific example embodiments are provided below. For example, a first embodiment includes a device for detecting an analyte within a sample, the device comprising: a metallic layer; and a plurality of dielectric pillars extending through the metallic layer, wherein a plurality of regions of concentrated light are supported in proximity to the ends of the plurality of dielectric pillars when a surface of the metallic layer is illuminated.

A second embodiment includes the device of any of the preceding device embodiments, further comprising a dielectric layer having a top surface and a bottom surface, wherein the metallic layer is formed on the top surface of the dielectric layer, and wherein the plurality of regions of concentrated light are supported in proximity to the ends of the plurality of dielectric pillars when the bottom surface of the metallic layer is illuminated.

A third embodiment includes the device of any of the preceding device embodiments, further comprising a window formed on the bottom surface of the dielectric layer below the plurality of dielectric pillars.

A fourth embodiment includes the device of any of the preceding device embodiments, wherein the plurality of regions of concentrated light comprise spatially-separated voxels above each of the plurality of dielectric pillars to which the light is substantially confined.

A fifth embodiment includes the device of any of the preceding device embodiments, wherein the electric field strength of the light decays exponentially with height above the plurality of dielectric pillars.

A sixth embodiment includes the device of any of the preceding device embodiments, wherein one or more of the plurality of dielectric pillars has a circular cross-section.

A seventh embodiment includes the device of any of the preceding device embodiments, wherein one or more of the plurality of dielectric pillars has a non-rotationally symmetric cross-section.

An eighth embodiment includes the device of any of the preceding device embodiments, wherein the plurality of dielectric pillars comprise a first pillar oriented with a first angular orientation, and a second pillar oriented with a different second angular orientation.

A ninth embodiment includes the device of any of the preceding device embodiments, wherein the plurality of dielectric pillars comprise a first pillar with a first cross-sectional aspect ratio, and a second pillar with a second cross-sectional aspect ratio.

A tenth embodiment includes the device of any of the preceding device embodiments, wherein the plurality of dielectric pillars have an average cross-sectional size greater than about 20 nm.

An eleventh embodiment includes the device of any of the preceding device embodiments, wherein the plurality of dielectric pillars have an average center-to-center spacing greater than about 100 nm.

A twelfth embodiment includes the device of any of the preceding device embodiments, wherein the metallic layer has a thickness of about 100 nm to about 500 nm.

A thirteenth embodiment includes the device of any of the preceding device embodiments, further comprising a light source configured to illuminate the bottom surface of the dielectric layer.

A fourteenth embodiment includes the device of any of the preceding device embodiments, further comprising an optical detector configured to receive light from an object located in one of the regions of concentrated light, the analyte being capable of being detected based on the received light.

A fifteenth embodiment includes the device of any of the preceding device embodiments, wherein the optical detector is located about 500 nm to about 100 microns from the plurality of dielectric pillars.

A sixteenth embodiment includes the device of any of the preceding device embodiments, wherein the optical detector comprises one or more lens elements for imaging the plurality of dielectric pillars.

A seventeenth embodiment includes the device of any of the preceding device embodiments, wherein the optical detector is capable of measuring detected light at a plurality of wavelengths.

An eighteenth embodiment includes the device of any of the preceding device embodiments, wherein the dielectric layer and the dielectric pillars comprise silicon or silicon dioxide.

A nineteenth embodiment includes the device of any of the preceding device embodiments, wherein metallic layer comprises gold or silver.

A twentieth embodiment includes the device of any of the preceding device embodiments, further comprising an analyte sample cell above, and in contact with, the plurality of dielectric pillars, the analyte sample cell being configured to receive a solution comprising an analyte of interest.

A twenty first embodiment includes the device of any of the preceding device embodiments, wherein the ends of the plurality of dielectric pillars extend beyond the top surface of the metallic layer or sit below the top surface of the metallic layer.

A twenty second embodiment includes the device of any of the preceding device embodiments, wherein the plurality of dielectric pillars are functionalized such that the plurality of dielectric pillars are capable of specifically binding to an analyte of interest.

A twenty third embodiment includes the device of any of the preceding device embodiments, wherein the plurality of dielectric pillars comprise a nucleic acid capture sequence or an antibody.

A twenty fourth embodiment includes the device of any of the preceding device embodiments, wherein the plurality of dielectric pillars are functionalized so as to form a pattern that becomes visible when the analyte is detected.

A twenty fifth embodiment includes an analyte detection method comprising: pumping an optical sensor with light, the optical sensor comprising a metallic layer, and a plurality of dielectric pillars extending through the metallic layer; and receiving light from the optical sensor to detect an analyte of interest in a sample located in proximity to the optical sensor.

A twenty sixth embodiment includes the method of any of the preceding analyte detection method embodiments, wherein pumping the optical sensor with light causes a plurality of regions of concentrated light in proximity to the ends of the plurality of dielectric pillars to be supported.

A twenty seventh embodiment includes the method of any of the preceding analyte detection method embodiments, wherein the light from the optical sensor comprises light from at least one of the regions of concentrated light.

A twenty eighth embodiment includes the method of any of the preceding analyte detection method embodiments, wherein the light from the optical sensor comprises light emitted from a labeled analyte molecule located within at least one of the regions of concentrated light.

A twenty ninth embodiment includes the method of any of the preceding analyte detection method embodiments, wherein the labeled analyte molecule is specifically bound to one of the dielectric pillars.

A thirtieth embodiment includes the method of any of the preceding analyte detection method embodiments, wherein the wavelength of the light with which the optical sensor is pumped is selected such that the plurality of regions of concentrated light span the entire thickness of the sample to allow for detection of unbound analyte molecules.

A thirty first embodiment includes the method of any of the preceding analyte detection method embodiments, further comprising measuring the light from the optical sensor at a plurality of wavelengths and detecting the analyte based on a change in the spectrum caused by the presence of the analyte within at least one of the regions of concentrated light.

A thirty second embodiment includes the method of any of the preceding analyte detection method embodiments, wherein pumping the optical sensor with light comprises using a broadband light source.

A thirty third embodiment includes the method of any of the preceding analyte detection method embodiments, wherein pumping the optical sensor with light comprises using a narrowband light source.

A thirty fourth embodiment includes the method of any of the preceding analyte detection method embodiments, wherein receiving light from the optical sensor comprises creating an image of a plane located at the ends of the plurality of dielectric pillars.

A thirty fifth embodiment includes the method of any of the preceding analyte detection method embodiments, wherein the plurality of dielectric pillars are sized to be smaller than the minimum detectable feature in the image.

A thirty sixth embodiment includes the method of any of the preceding analyte detection method embodiments, wherein the plurality of dielectric pillars comprise individual dielectric pillars having a non-rotationally symmetric cross-section, the individual dielectric pillars being arranged in a plurality of different angular orientations, the method further comprising: pumping the plurality of dielectric pillars using light having a first polarization angle; receiving light from the optical sensor to detect the analyte of interest while pumping the plurality of dielectric pillars using light having the first polarization angle; pumping the plurality of dielectric pillars using light having a different second polarization angle; receiving light from the optical sensor to detect the analyte of interest while pumping the plurality of dielectric pillars using light having the second polarization angle; and analyzing images of the light received from the optical sensor to determine the location of the analyte.

A thirty seventh embodiment includes the method of any of the preceding analyte detection method embodiments, wherein the plurality of dielectric pillars comprise individual dielectric pillars having a non-rotationally symmetric cross-section with a plurality of different aspect ratios, the method further comprising: pumping the plurality of dielectric pillars using light having a first wavelength; receiving light from the optical sensor to detect the analyte of interest while pumping the plurality of dielectric pillars using light having the first wavelength; pumping the plurality of dielectric pillars using light having a different second wavelength; receiving light from the optical sensor to detect the analyte of interest while pumping the plurality of dielectric pillars using light having the second wavelength; and analyzing images of the light received from the optical sensor to determine the location of the analyte.

A thirty eighth embodiment includes a method of fabricating an optical sensor, the method comprising providing a substrate; etching a plurality of pillars into a top surface of the substrate; applying a metallic layer over the plurality of pillars and the substrate; and etching a window beneath the plurality of pillars into the bottom surface of the substrate.

A thirty ninth embodiment includes the method of any of the preceding method of fabrication embodiments, wherein the substrate comprises silicon.

A fortieth embodiment includes the method of any of the preceding method of fabrication embodiments, further comprising oxidizing the silicon to convert the pillars and at least a portion of the substrate into silicon dioxide.

A forty first embodiment includes the method of any of the preceding method of fabrication embodiments, further comprising removing metal from the sidewalk of the plurality of pillars by heating the metallic layer, thus causing it to reflow.

A forty second embodiment includes the method of any of the preceding method of fabrication embodiments, further comprising applying mechanical force to break off at least a portion of the plurality of dielectric pillars that extend above the top surface of the metallic layer.

BRIEF DESCRIPTION OF THE DRAWINGS

For purposes of summarizing the disclosure, certain aspects, advantages and features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein. Certain embodiments are illustrated in the accompanying drawings, which are for illustrative purposes only.

FIG. 3A is a schematic illustration of another example dielectric pillar for the optical sensor of FIG. 1.

FIG. 3B is an illustration of a computer simulation of the electric field strength of light in and around the dielectric pillar illustrated in FIG. 3A.

DETAILED DESCRIPTION

Figure 1:
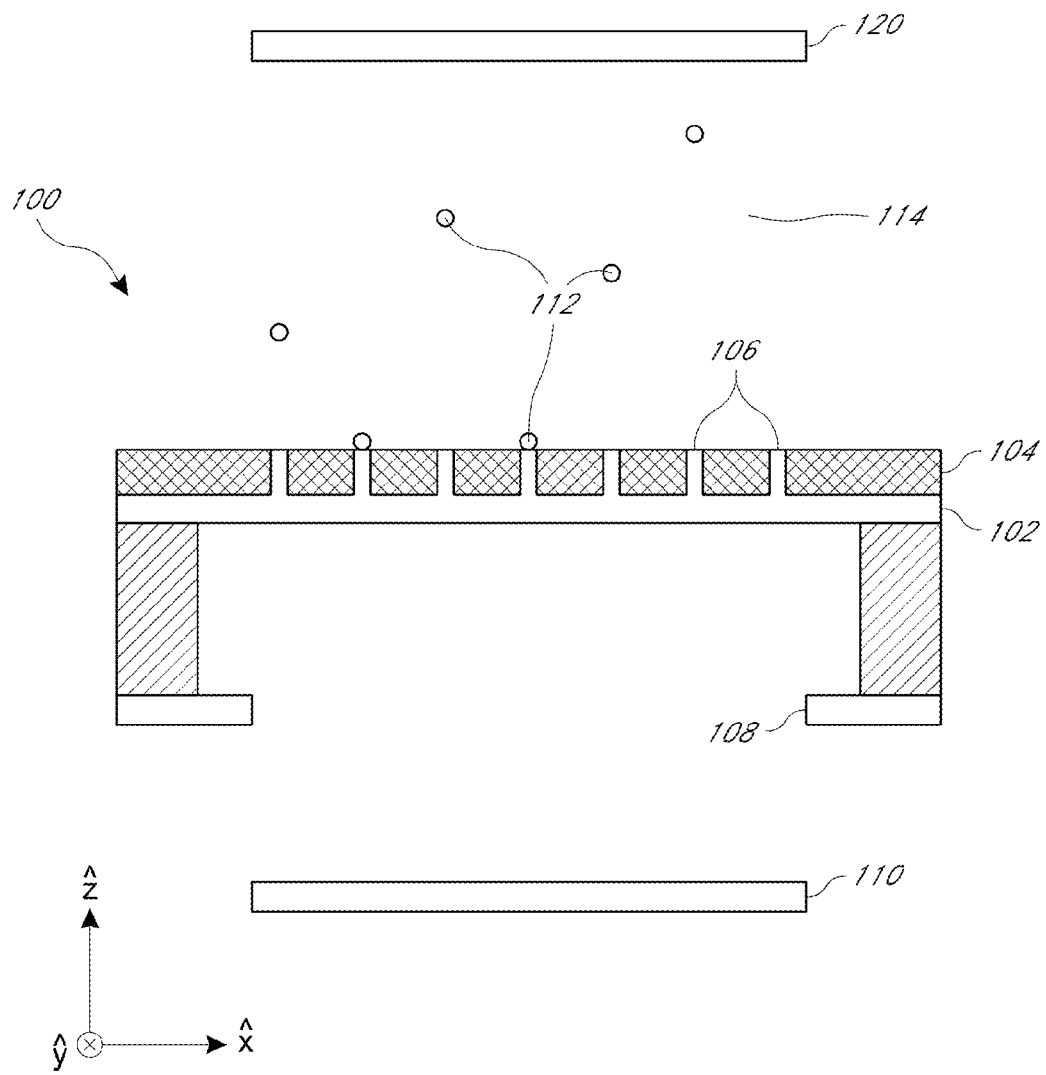
FIG. 1 is a schematic illustration of an optical sensor for detecting an analyte in a sample.

FIG. 1 is a schematic illustration of an optical sensor 100 for detecting an analyte 112 in a sample 114. In some embodiments, the optical sensor 100 is part of a detection system that also includes a light source 110 and an optical detector 120. The analyte-containing sample 114 can be, for example, a fluid that is in physical contact with the top surface of the metallic layer 104 and the dielectric pillars 106.

The optical sensor 100 can include a dielectric layer 102. The dielectric layer 102 can be a planar layer (illustrated in the XY plane of FIG. 1) of dielectric material, such as, for example, silicon or silicon dioxide. Other dielectric materials can also be used, including, for example, silicon nitride and aluminum oxide. The thickness of the dielectric layer 102 can be, for example, between about 10 nm and about 2000 nm, though other thicknesses are also possible. A metallic layer 104 can be provided on or adjacent the top surface of the dielectric layer 102. The metallic layer 104 can be a planar layer of metal, such as, for example, gold. Other metals can also be used, including silver, copper, and aluminum. In some embodiments, the metallic layer 104 can consist of multiple sub-layers of different metals. For example, a relatively thin layer of titanium can be provided on the top surface of the dielectric layer 102 to aid in adhesion of a layer of gold formed on top of the layer of titanium. The thickness of the metallic layer 104 can be, for example, between about 100 nm and about 500 nm, though other thicknesses are also possible. Although the embodiment illustrated in FIG. 1 includes the dielectric layer 102, this layer is not required in all embodiments.

A plurality of dielectric pillars 106 can also be provided on or adjacent the top surface of the dielectric layer 102. In some embodiments, the dielectric pillars 106 are nano-scale structures, as discussed further herein. The dielectric pillars 106 can be formed of for example, the same material as the dielectric layer 102. In addition, the dielectric pillars 106 can be integral with the dielectric layer 102. The dielectric pillars 106 can serve as optically transmissive apertures through the metallic layer 104. As a result, the terms "pillars" and "apertures" are both used in this disclosure to refer to these structures. In some embodiments, the dielectric pillars 106 extend partially or completely through the metallic layer 104. As illustrated in FIG. 1, the height of the dielectric pillars 106 can be the same as the thickness of the metallic layer 104, such that the ends of the dielectric pillars (distal from the dielectric layer 102) are flush with the top surface of the metallic layer 104. However, in other embodiments, the ends of the dielectric pillars 106 may protrude above, or sit below, the top surface of the metallic layer 104. The distal ends of the dielectric pillars 106 are referred to as "pads" elsewhere in this disclosure.

A light source 110 can be provided below the optical sensor 100 and can be used to provide pumping light. In some embodiments, the light source 110 can be used to illuminate the bottom surface of the dielectric layer 102. As illustrated in FIG. 1, a window 108 can be provided below the dielectric layer 102. The window 108 can be registered with the dielectric pillars 106 so as to allow light from the light source 110 to reach the dielectric layer 102 and/or the metallic layer 104 in the region of the dielectric pillars 106 but otherwise mask the illumination from the light source 110. The light source 110 can have a narrowband or broadband wavelength range of emission, depending upon the particular application, as discussed further herein. The light source 110 can be, for example, a laser, a light emitting diode (LED), a lamp, etc., or even natural sunlight. In some embodiments, the light source 110 emits infrared, visible, and/or ultraviolet light.

As discussed further herein, when the light source 110 illuminates the bottom surface of the dielectric layer 102, light is transmitted through the dielectric layer 102 and the dielectric pillars 106. However, by the principle of surface plasmon resonance, the presence of the metallic layer 104, in conjunction with the shapes, sizes, and patterns of the dielectric pillars 106, causes light to be concentrated in voxels located above and adjacent the ends of the dielectric pillars 106. Advantageously, because of the surface plasmon resonance, light can be focused to a volume having one or more dimensions that are smaller than the wavelength of the light or any diffraction limit associated with the wavelength of the light. In some embodiments, the volume of concentrated light has cross-sectional dimensions of about $\lambda/500$ to about $\lambda/5$ per side, and a longitudinal dimension of about $\lambda/500$ to about $\lambda/5$, where $\lambda$ is the center wavelength of the pumping light.

The dielectric pillars 106 can serve as nano-apertures through the metallic layer that can be used to pump near-field sub-diffraction volumes, and to serve as a two-dimensional imaging plane for chemical/biological sensing applications. For example, as discussed further herein, the areas of focused or concentrated light can allow the optical detector 120 to detect an analyte 112 that is present within a sample 114 that is provided between the optical sensor 100 and the optical detector 120. Since the areas of concentrated light can be smaller than the size of, for example, a laser beam focused by a lens (as may be used in other detection systems), the optical sensor 100 can be capable of detecting the location of an analyte within a sample with relatively high spatial resolutions.

Figures 2A, 2B:
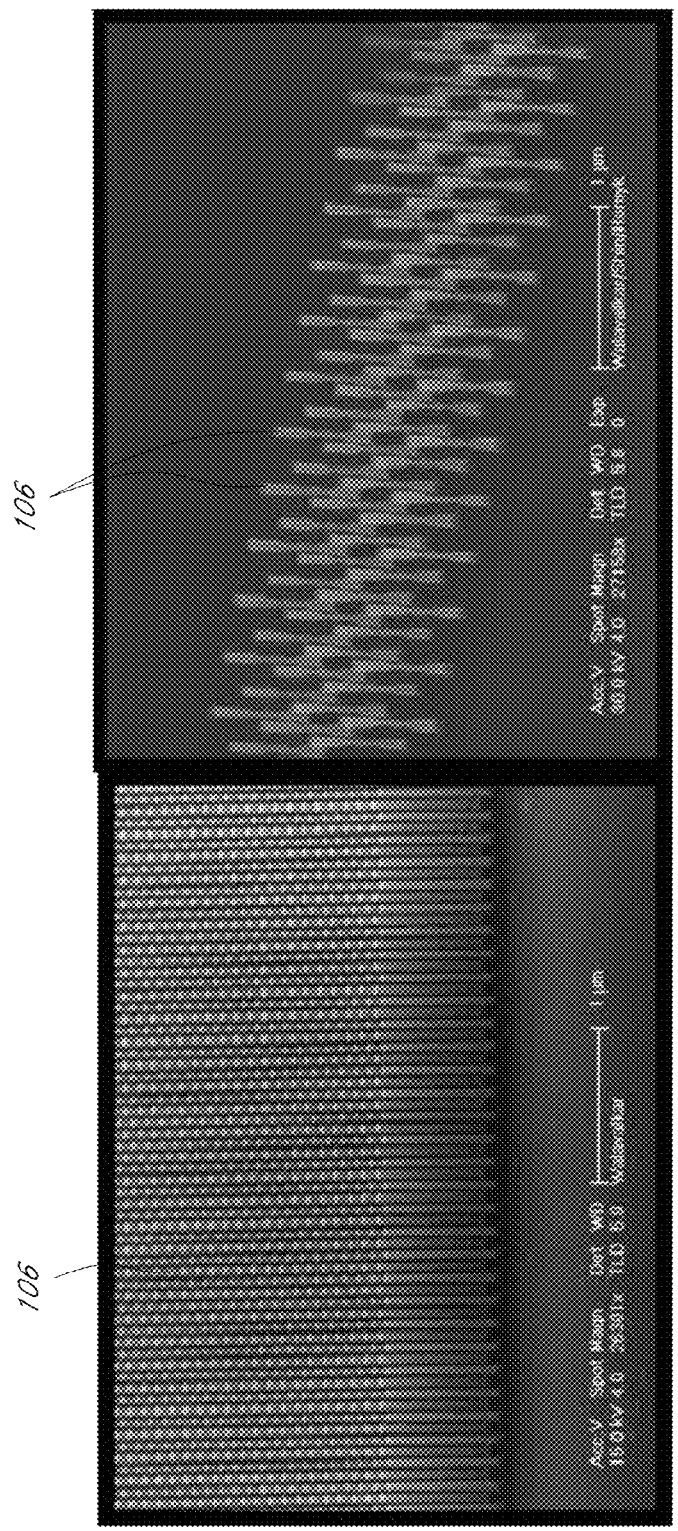
FIG. 2A is a scanning electron microscope image of example dielectric pillars for the optical sensor of FIG. 1.
FIG. 2B is another scanning electron microscope image of example dielectric pillars.

FIG. 2A is a scanning electron microscope image of example dielectric pillars 106 for the optical sensor 100 of FIG. 1. The dielectric pillars 106 in this image have a circular cross-section, though this is not required in all embodiments. For example, the dielectric pillars 106 can be designed to have cross-sections that are square, rectangular, ellipsoidal, or any other desired shape. In addition, the dielectric pillars 106 in FIG. 2A have vertical sidewalls, though this is also not required in all embodiments.

As already mentioned, the dielectric pillars 106 can be nano-scale structures. The average cross-sectional dimensions (e.g., diameter) for each of the dielectric pillars 106 can be, for example, 20 nm or more, though smaller structures may also be useful. In some embodiments, the average center-to-center spacing between neighboring dielectric pillars 106 can be, for example, between about 100 nm and several microns. Other sizes and spacings are also possible, and may vary depending upon the wavelength of light being used in the optical sensor 100 to detect the analyte of interest. For example, in some embodiments, the cross-sectional dimensions may larger than $\lambda/500$, where $\lambda$ is the center wavelength of the pumping light, but smaller than $\lambda/2$. In some embodiments, the cross-sectional dimensions of the dielectric pillars 106 can be, for example, on the order of the smallest resolvable spot size of the optical detector 120 for the wavelength of light in question, or smaller. As illustrated in FIG. 2A, the dielectric pillars 106 can be provided in a two-dimensional array. The dielectric pillars 106 can be laid out in any suitable lattice structure, including square, hexagonal, etc. Irregular patterns can also be used in some embodiments.

FIG. 2B is another scanning electron microscope image of example dielectric pillars 106. Unlike those illustrated in FIG. 2A, the dielectric pillars 106 in FIG. 2B do not have vertical sidewalls. Instead, the sidewalls are sculpted such that the dielectric pillars 106 are tapered in the middle. In other embodiments, the sidewalls of the dielectric pillars 106 can be sculpted such that the pillars are tapered at the top or at the bottom. More complex shapes are also possible. The sculpting of the sidewalls of the dielectric pillars can be controlled by modifying etching parameters, as discussed herein.

FIG. 3A is a schematic illustration of another example dielectric pillar 106 for the optical sensor of FIG. 1. The dielectric pillar 106 is integral with the dielectric layer 102 and serves as an optically transmissive aperture through the metallic layer 104. A fluid sample 114 is also illustrated in FIG. 3A above and in contact with the dielectric pillar 106. In some embodiments the optical sensor 100 can include suitable structures (e.g., walls) to receive and contain the fluid sample. As illustrated in FIG. 3A, the dielectric pillar 106 in this example is tapered such that it has a first diameter at its base, and a second, narrower diameter at its tip.

FIG. 3B is an illustration of a computer simulation of the electric field strength of light in and around the dielectric pillar 106 illustrated in FIG. 3A. FIG. 3B illustrates the electric fields that results when the bottom surface of the dielectric layer 102 is illuminated by the light source 110, with lighter areas generally corresponding to higher field strengths. Of particular interest in FIG. 3B is the area of concentrated light 107 located above the pad of the dielectric pillar 106. As illustrated, the concentrated light 107 is substantially spatially confined in the XY plane based on the cross-sectional dimensions of the dielectric pillar 106. In addition, the concentrated light 107 is substantially spatially confined in the Z direction to the space above the dielectric pillar 106. In this particular computer simulation, the dielectric pillar 106 had a diameter of about 50 nm at its base and about 25 nm at its tip. The thickness of the gold metallic layer 104 was 250 nm. The spacing between adjacent dielectric pillars was 500 nm. The dielectric pillar 100 illustrated in FIG. 3B was pumped with light having a wavelength of 405 nm, and the concentrated light 107 was substantially confined to a 25 nm×25 nm×25 nm voxel above the tip of the dielectric pillar 106. The boundaries of the region 107 of concentrated light can be defined, for example, by the space within which the electric field of the light is at least about 70% of the maximum value of the electric field (about 50% power) in the space above the pad of the dielectric pillar 17. As discussed further herein, the extent of the region 107 of concentrated light in the Z direction can advantageously be controlled based upon the transmissivity of the wavelength of light used to pump the optical sensor 100.

Figure 4:
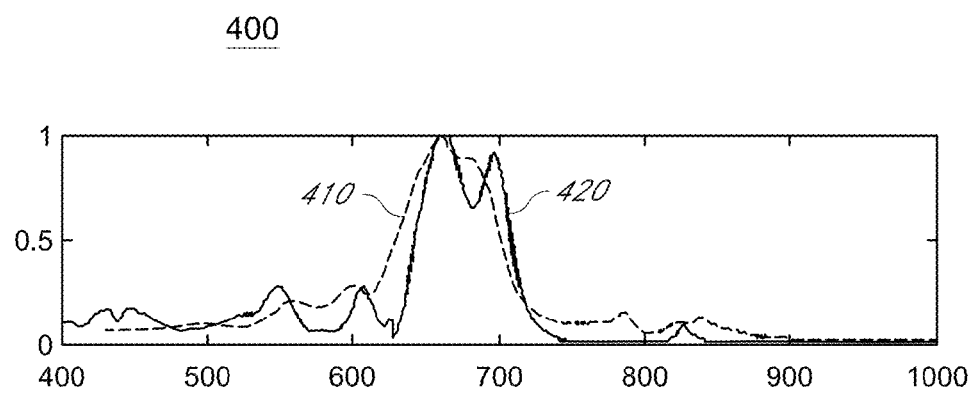
FIG. 4 is a graph that shows the transmission spectrum for an example set of dielectric pillars in an optical sensor of the type illustrated in FIG. 1.

FIG. 4 is a graph 400 that shows the transmission spectrum for an example set of dielectric pillars 106 in an optical sensor 100 of the type illustrated in FIG. 1. FIG. 4 plots normalized transmission as a function of wavelength. Each set of dielectric pillars, or apertures through the metallic layer 104, has a distinct transmission spectrum that is a function of, for example, aperture size, spacing, and metallic layer thickness. In the example illustrated in FIG. 4, the optical sensor 100 has a metallic layer thickness of 300 nm of gold. The dielectric pillars 106 have a diameter of 180 nm, and are arranged in a square lattice with a spacing of 750 nm between closest neighboring pillars. The graph 400 shows the transmission spectrum for wavelength of light from 400 nm to 1000 nm. The graph 400 includes a dashed trace 410 that illustrates the experimental transmission spectrum. The graph 400 also includes a solid trace 420 that corresponds to the theoretical transmission spectrum.

As illustrated in FIG. 4, for this particular example, the transmission of the dielectric pillars 106 is the highest from approximately 650 nm to approximately 700 nm. On either side of this peak, the transmission of light through the apertures is substantially less. As discussed further herein, the variation in optical transmission at different wavelengths can be used to control the Z direction extent of the region 107 of concentrated light above each of the dielectric pillars 106.

Figure 5:
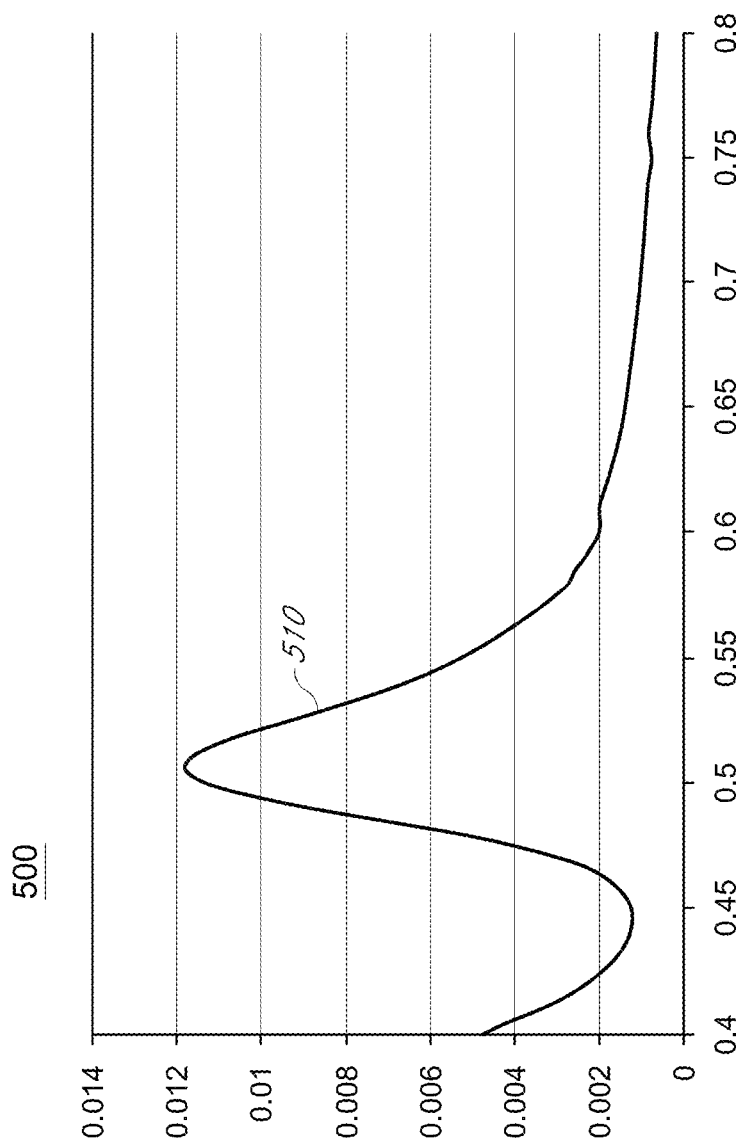
FIG. 5 is a graph that shows the transmission spectrum for another example set of dielectric pillars in an optical sensor of the type illustrated in FIG. 1.

FIG. 5 is a graph 500 that shows the transmission spectrum for another example set of dielectric pillars 106 in an optical sensor 100 of the type illustrated in FIG. 1. Like FIG. 4, FIG. 5 plots transmission (not normalized) as a function of wavelength (here, measured in microns rather than nanometers). In the example illustrated in FIG. 5, the dielectric pillars 106 were tapered, having a diameter of 50 nm at their bases and 25 nm at their tips. The inter-pillar spacing was 500 nm, and the metallic layer 104 was a layer of gold having a thickness of 250 nm. The graph 500 shows the transmission of the optical device from 400 nm to 800 nm.

Figure 6:
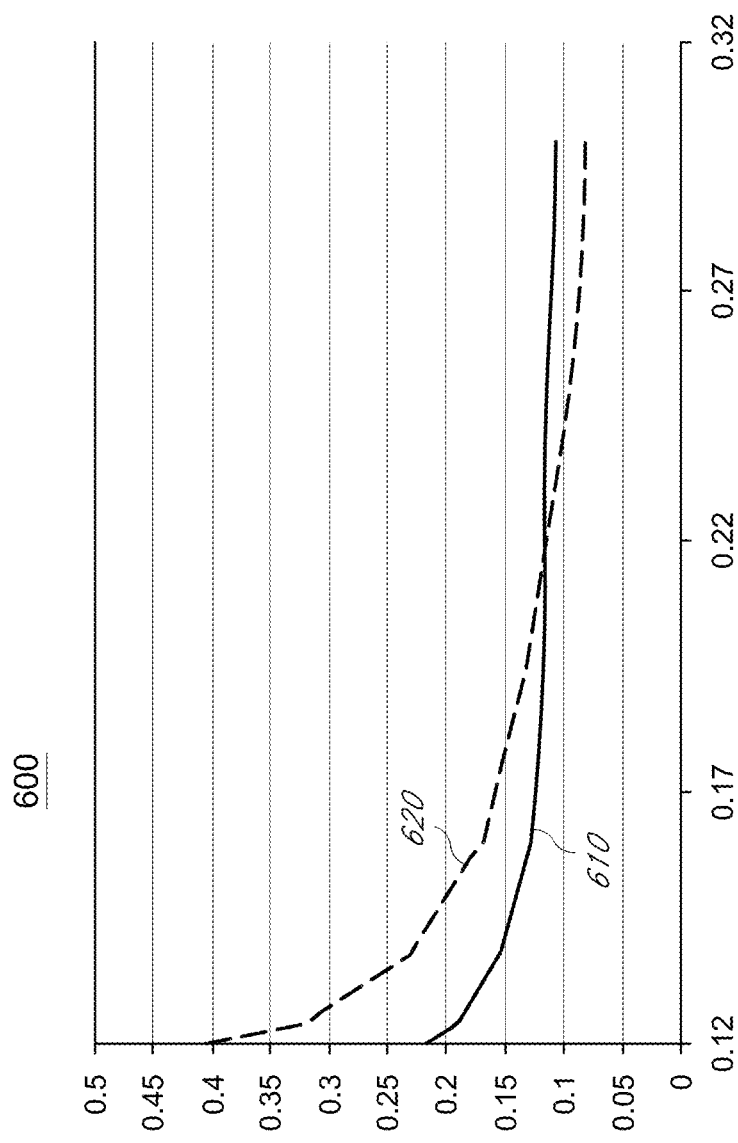
FIG. 6 is a graph showing the electric field strength of light above an example dielectric pillar as a function of distance in the Z direction.

FIG. 6 is a graph 600 showing the electric field strength of light above an example dielectric pillar as a function of distance in the Z direction. The Z distance is plotted in microns. (In this example, 0.12 on the X scale represents the top of the dielectric pillars 106.) The graph 600 has a solid curve 610 that represents light having a wavelength of 500 nm, while the dashed curve 620 represents light having a wavelength of 405 nm. As illustrated in FIG. 6, the electric field strength of the light generally decreases exponentially with increasing distance above the top of the dielectric pillars 106.

In general, wavelengths of light that are more poorly transmitted through the apertures with lower transmission values are more tightly confined to the pads of the dielectric pillars 106, while wavelengths of light with higher transmission values are less tightly confined. In the particular cases illustrated in FIG. 6, the transmission of the 500 nm light through the optical sensor 100 was greater than the transmission of the 405 nm light. This can be seen in FIG. 6, where the exponential decay of the electric field of the 405 nm light (dashed curve 620) is steeper (with a more intense peak). In contrast, the exponential decay of the 500 nm light (solid curve 610) is flatter (with a less intense peak), thus extending the region 107 of concentrated light further in the Z direction above the pads of the dielectric pillars 106. Depending upon the disparity between the transmission of two different wavelengths of light through the apertures 106, the region 107 of concentrated light can be, for example, on the order of microns higher for the wavelength of light that has a higher transmission value as compared to the wavelength of light that is transmitted more poorly.

As discussed herein, the data illustrated in FIG. 6 show that the extent to which the region 107 of concentrated light for a particular wavelength extends in the Z direction is dependent upon how well that wavelength is transmitted by the optical sensor 100. Thus, the pumping wavelength of light can be selected so as to control the height of the regions of concentrated light 107. In some applications, it may be desirable to have relatively small regions of concentrated light 107, in which case a wavelength of light that is relatively poorly transmitted can be used. In other applications, larger regions of concentrated light 107 may be desirable, in which case a wavelength of light with better transmission can be used.

As explained further herein, an analyte in a sample located in proximity to the optical sensor 100 can be detected by pumping the optical sensor with light. This can be done, for example, by illuminating the bottom surface of the dielectric layer 102 and/or the metallic layer 104. An optical detector can be used to receive light from the optical sensor to detect the analyte of interest. The optical detector can, for example, create an image of a detection plane located at or near the apertures 106. The image can be analyzed by a computer in order to detect, for example, bright regions that correspond to the presence of an analyte molecule.

Figure 7A:
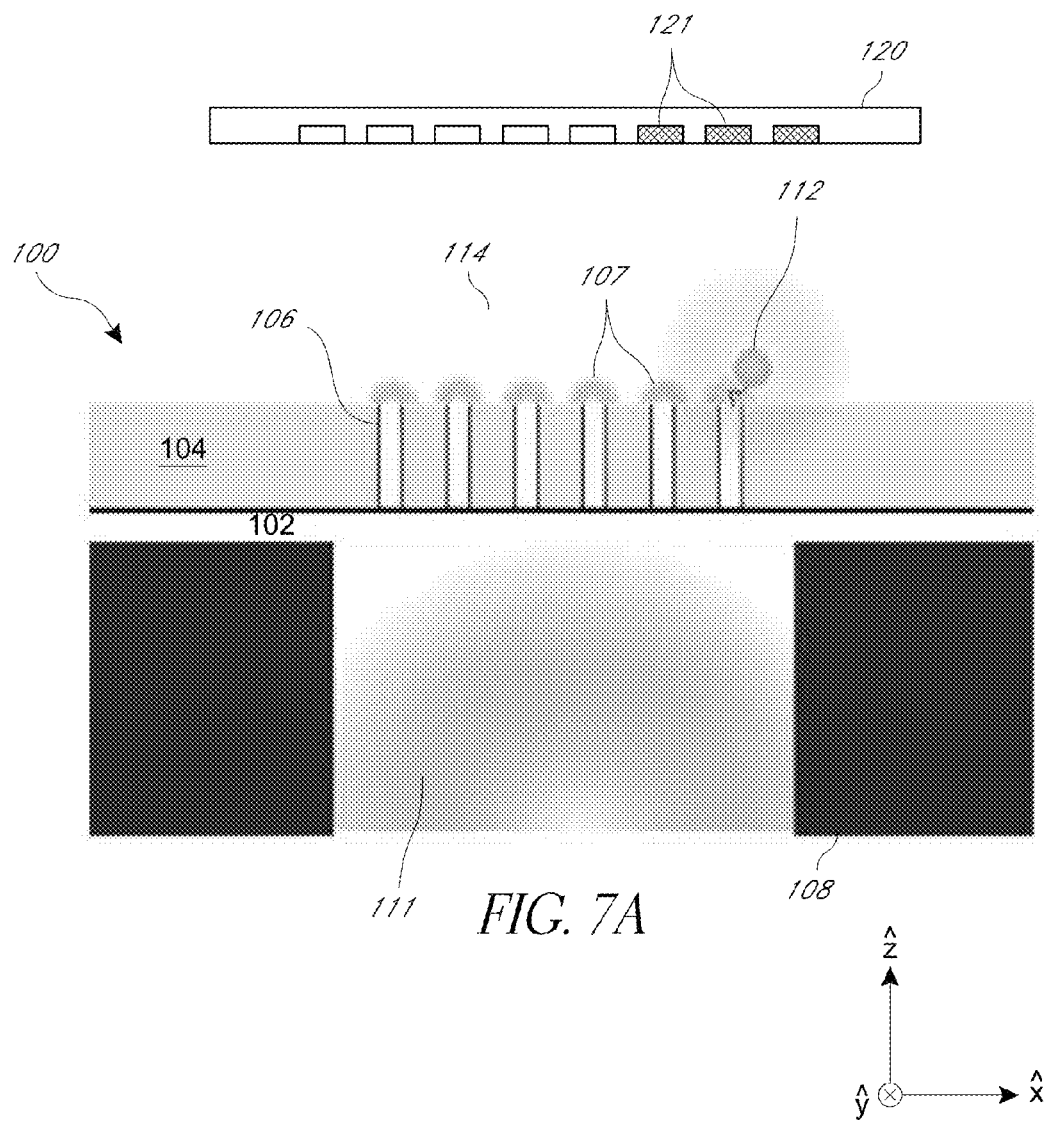
FIG. 7A illustrates an embodiment of analyte detection using the optical sensor of FIG. 1.

FIG. 7A illustrates an embodiment of analyte detection using the optical sensor 100 of FIG. 1. FIG. 7A illustrates the optical sensor 100, including the dielectric layer 102, the metallic layer 104, and the plurality of dielectric pillars 106. The optical sensor 100 is adjacent to a sample 114 that includes an analyte 112 that is to be detected. As discussed further herein, the analyte 112 can be a fluorescently-labeled molecule (as illustrated in FIG. 7A). The optical sensor 100 is illustrated as being pumped with light 111 from a light source 110 (not shown). This optical pumping results in regions of concentrated light 107 above each of the dielectric pillars 106, as discussed herein.

An optical detector 120 can be located above the optical sensor 100. The optical detector can be, for example, a microscope for magnifying and imaging an XY plane located at or near the pads of the dielectric pillars 106. The optical detector can also include an array of photo detector elements 121, such as a CCD or CMOS sensor, and can be coupled to a computer for recording and analyzing the digital image data from the photo detector array to characterize the analyte by determining, for example, the presence and/or location of an analyte molecule or particle. In some embodiments, the optical detector 120 includes an array of photo detector elements 121 without imaging optics.

As discussed herein, light transmitted through the apertures 106 is confined to regions 107 just above the pads of the dielectric pillars. If the optical detector 120 is located in the Z direction beyond the regions 107 where light is confined, then relatively little light reaches the optical detector 120. Thus, even while the optical sensor 100 is being pumped with light 111 from a light source 110, the optical detector 120 would image a dark plane.

In some embodiments, however, the dielectric pillars 106 are functionalized to specifically bind to the analyte 112 of interest in the sample 114. If the analyte 112 is fluorescently-labeled (using, for example, green fluorescent protein), then an analyte molecule 112 that is specifically bound to a dielectric pillar 106 can optically interact with the region of concentrated light 107. In the case of a fluorescently-labeled molecule, this interaction would result in the emission of light by fluorescence that could then be detected by the optical detector 120 as appearing to cause one of the apertures 106 to light up. The image collected by the optical detector 120 would show a relatively bright spot at one or more image pixels that correspond to the location of the dielectric pillar 106 to which the fluorescing analyte molecule is specifically bound. In some embodiments, the analyte of interest is a protein or DNA molecule, though many other analytes of interest could be detected using the optical sensor 100.

Using this technique, it is possible to detect the presence and location of a binding event between the analyte of interest and a given dielectric pillar 106 using, for example, a bright versus dark, on versus off, detection scheme. The confinement of light near the surface of the dielectric pillars can be advantageous in some embodiments because the confinement of light may help to ensure that the pumping light 111 only excites labeled analyte molecules that are bound to the surface of a dielectric pillar 106 and not freely floating in the sample solution 114 beyond the regions of concentrated light 107. However, in other embodiments, it may be advantageous to be able to detect free-floating analyte molecules in the sample solution, as discussed herein.

Figure 7B:
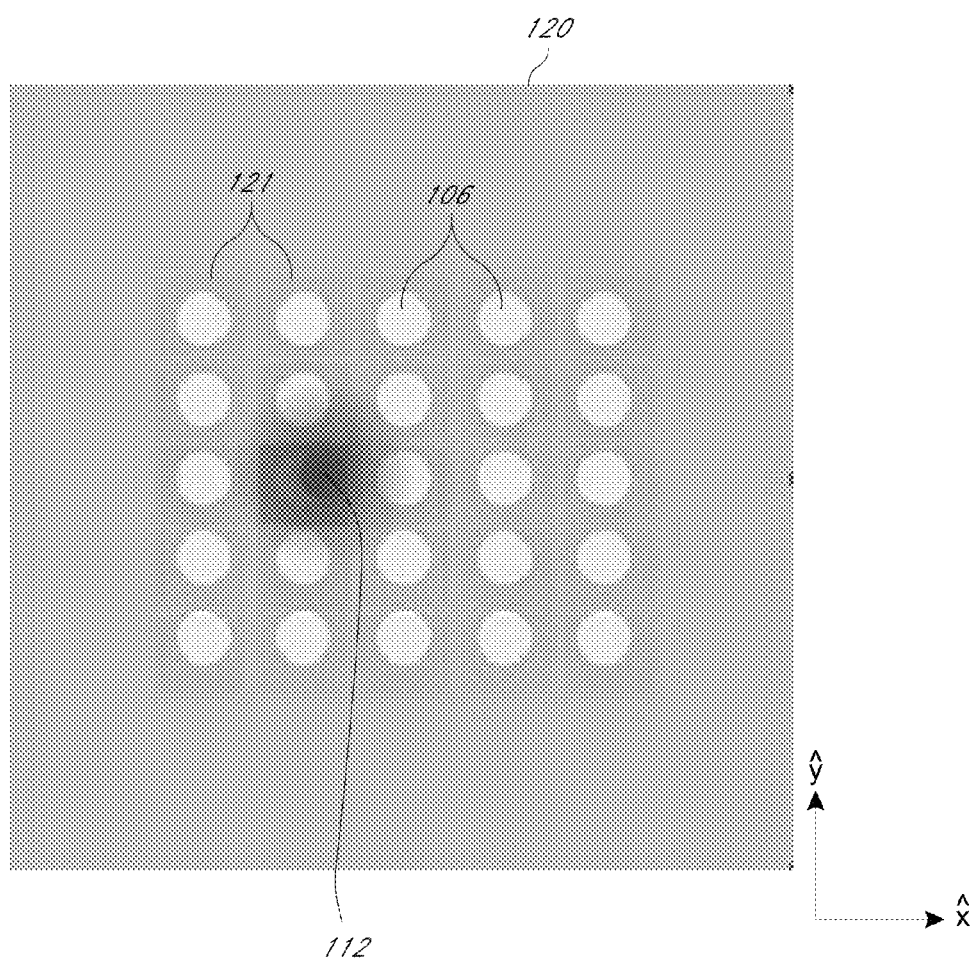
FIG. 7B illustrates a top view of the detection system used in the analyte detection embodiment of FIG. 7A.

FIG. 7B illustrates a top view of the detection system used in the analyte detection embodiment of FIG. 7A. In particular, FIG. 7B shows the optical detector 120 and the array of photodetector elements 121. These may be, for example, pixels of a CMOS or CCD sensor. Signal light can be collected from the aperture array and be imaged by the array of photodetector elements 121. In some embodiments, relay optics are omitted and the imaging device is placed proximal to the aperture array. In some embodiments, the optical detector 120 is located about 500 nm or more above the array of apertures 106 in the Z direction. In some embodiments, the distance is less than 100 microns. For example, the distance may be 1-2 microns. Other distances can also be used, however, depending upon the application.

In some embodiments, the respective pitches of the aperture and detector arrays are substantially similar, so that each aperture 106 is aligned with a single pixel of the detector imaging device. Current cameras, such as those that are used in certain smart phones, have a pixel pitch of 1-3 microns. In such a case, the array of dielectric pillars 106 could likewise have a 1-3 micron pitch, and the separation between the apertures 106 and detector array could be on the order of 1-3 microns, as well.

In other embodiments, however, the pitch of the array of apertures 106 can be larger than the pitch of the array of photodetector elements 121. In some embodiments, the optical detector 120 may have an arrangement of photodetector elements 121 that associates, for example, $n^2$ (e.g., 9) photodetector elements 121 with each aperture 106. In such a case, the pitch of the aperture array could be n (e.g., 3) times that of the detector array. Various arrangements of the photodetector elements 121 with an n×n photodetector pixel set associated with each aperture 106 are possible and useful.

In some embodiments, the apertures 106 can be spaced apart from each other by about 3 times the pitch of the photodetector elements 121. In this way, the optical detector 120 can be located about 3 times the pitch of the photodetector elements 121 from the apertures 106 and can capture the fluorescence from a detected analyte molecule 112 on a 3×3 grid of pixels (e.g., the 3×3 grid of photodetector elements 121 surrounding the detected analyte molecule 112 in FIG. 7B). The actual location of the detected analyte molecule 112 could be determined from for example, the centroid of the signal from the 3×3 grid. In one example, a reasonable pixel pitch on an inexpensive CMOS camera is about 3 microns. In this example, the apertures 106 could be spaced with a pitch of about 9 microns and the CMOS array could likewise be spaced apart from the apertures 106 by about 9 microns. Many other configurations are also possible.

Figure 8:
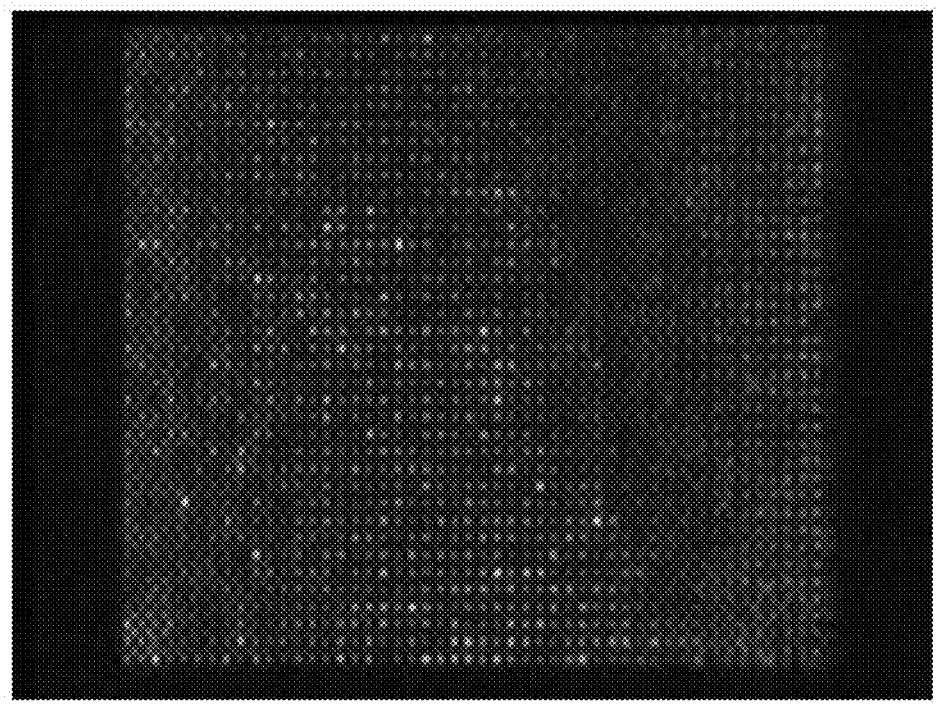
FIG. 8 is an example image from an optical sensor that can be used to detect analyte molecules or particles that are not specifically bound to dielectric pillars.

FIG. 8 is an example image 800 from an optical sensor that can be used to detect analyte molecules or particles that are not specifically bound to dielectric pillars. As discussed herein, when a wavelength of light that is relatively poorly transmitted by the apertures 106 is used to pump the optical sensor 100, the transmitted light is focused to relatively small regions 107 of confinement near the pads of the dielectric pillars 106. In such cases, an image of the plane of the dielectric pillars 106 collected by the optical detector 120 is simply a dark frame unless a fluorescently-labeled analyte molecule or particle 112 is specifically bound to one or more of the dielectric pillars 106. However, by selecting a wavelength of light with relatively strong transmission through the apertures 106, the size of the regions 107 of confinement can be extended in the Z direction by, for example, several microns. Thus, if the analyte-containing sample 114 is less than several microns thick, the regions of concentrated light 107 can be designed to span the entire sample in the Z direction by selection of an appropriate wavelength of pumping light.

FIG. 8 is an example of the illumination pattern 800 that would result from this technique. FIG. 8 consists of an array of columns of illumination (each corresponding to an aperture 106) whose cross-sectional dimensions can be individually smaller than a laser beam can be focused using a lens. Any fluorescently-labeled analyte molecule or particle 112 that is located in the sample 114 within one of these illuminated columns can be excited and made to fluoresce. The fluorescence can then be detected by the optical detector 120 to identify the presence and location of the analyte. Accordingly, an entire sample cell can be imaged simultaneously with greater spatial resolution than is possible from using, for example, a lens-focused scanning laser beam to interrogate the analyte sample 114.

Although the optical sensor 100 can be used to detect fluorescently-labeled analyte molecules, in some embodiments, it is not necessary to use fluorescent labeling for detection. For example, the highly confined nature of the light above the dielectric pillars 106 means that the light can interact strongly with any molecule or particle that is located in or near a portion of the electric field of the concentrated light (e.g., by specifically binding to one of the dielectric pillars 106). This interaction can have the effect of shifting the transmission spectrum of the light, which can then be measured and quantified in order to detect the presence of analyte molecules or particles. This detection method can be used to detect passive or untagged objects, such as nanoparticles or large proteins.

In some embodiments, the optical sensor 100 is pumped with a broadband light source (e.g., white light). In such embodiments, the optical detector 120 can be a spectrometer that is located near enough to the regions of concentrated light 107 in order to analyze the spectrum of broadband light transmitted through one or more of the apertures 106. The spectrometer can be used to measure the intensity of the transmitted spectrum as a function of wavelength. The presence of analyte molecules or particles that are specifically bound to one or more pillars 106 can change the shape of the transmitted spectrum in a measurable way that allows for detection of the analyte molecule or particle. (The optical detector 120 need not necessarily be located within the regions of concentrated light 107 in order to measure the transmitted spectrum because the presence of a bound particle at a dielectric pillar 106 can cause light to be scattered and become detectable outside the normal region of concentrated light.)

In some embodiments, this method may be particularly effective when a sizable portion of the pillars 106 have analyte molecules or particles present, as the spectrometer reading may be dependent on the interaction of a relatively large number of apertures 106 rather than a single one. Thus, this method may be particularly useful when binding events are likely and there is a good chance of saturating the pillars/apertures.

In some embodiments, a multi-channel detector array (e.g., a red-green-blue (RGB) CCD or CMOS detector array) can be used to analyze the spectral signature of the light from the apertures 106. The multi-channel detector array can be positioned near enough to the array of pillars 106 such that light from the regions of concentrated light 107 can be detected. The multi-channel detector array can optionally be paired with optics that focus light from each aperture to one or more detector pixels. Alternatively, optics can be excluded and the pitch of the pixels in the detector array can be, for example, the same as, or greater than, the pitch of the apertures 106. In this way, one or more detector pixels can correspond to each of the apertures 106.

When an analyte molecule or particle is not present at a pillar 106, the corresponding detector pixel(s) will have a certain measurable value in each wavelength detection channel (e.g., red, green, and blue wavelengths). When an analyte molecule or particle perturbs the light output at an aperture 106, the relative intensity of light in each wavelength detection channel may shift based on the shift in the transmission spectrum of the aperture. Therefore, the presence of an analyte molecule or particle can be detected as a "color change" by the multi-channel detector. Alternatively, a single channel detector can be used when, for example, the optical sensor 100 is pumped with a narrowband light source. The transmission of the narrowband light source at each aperture 106 can have one value (e.g., a relative minimum or maximum) in the absence of a bound analyte molecule or particle. When an analyte molecule or particle is present at the pillar 106, the transmission of the narrowband light source can be shifted to have a new value. For example, a relative transmission minimum could be shifted to a relative maximum, or vice versa. In this way, it may be possible to measure the presence of an analyte molecule or particle based on a "dark" aperture 106 at the pumping wavelength becoming "lit," or vice versa.

As discussed herein, one or more of the dielectric pillars 106 can be functionalized so as to specifically bind with an analyte of interest. Each pillar can be composed of a dielectric material. The properties of the dielectric material may help determine both the optical characteristics of the aperture array and to its use in biological assays. One such material that is used in some embodiments is silicon dioxide, or silica ($SiO_2$).

The assay reaction can occur on the pads of the dielectric pillars 106. One assay of some embodiments is a binding assay, wherein a chemical modification is made to one or more of the pads so that an analyte 112, when presented in a fluid sample 114 applied to the top surfaces of the pillars 106, may localize to the pad for subsequent detection.

In some embodiments, pads can be derivatized so that they present a different nucleic acid capture sequence; the fluid may contain target nucleic acids, each of which may carry an optically detectable label. The target nucleic acids specifically attach to the capture sequences on the pads. Illumination of the back side of the optical sensor 100 can result in detectable radiation indicative of the presence of the labeled target nucleic acid on the respective pad, as discussed herein.

The derivatization of the pad may involve silanization of the silica with compounds that have specific attachment groups for binding the capture nucleic acids. The detection may be of the fluorescence emitted by a label on the target nucleic acid, or of increased/decreased transmission of the pumping light as a consequence of the presence of a plasmonic-particle label on the target nucleic acid. Whether fluorescence, luminescence, or modified transmission of pumping radiation, this light is the "signal" that allows for detection of the analyte.

Other chemistries can also be used, such as the following:

Nucleic acid sequencing—Sequencing by synthesis, wherein the target nucleic acid strands can be attached to the pads and those immobilized strands can have a double stranded region formed by a primer and the target strand allowing labeled nucleotides complementary to the immobilized strand to be incorporated one by one to the primer.

Immunoassays—Antibodies can be immobilized on the pads; the analyte in the fluid can bind to the antibody and a second labeled antibody binds to the analyte. The amount of labeled antibody on the pad can then be measured.

Pathogen detection—Some embodiments of pathogen detection can be based on the general description of nucleic acid detection described above. Nucleic acids in a sample can be labeled and introduced into the device. If pathogen nucleic acids are in the sample, the corresponding labeled DNA will bind to the complementary, pathogen-specific capture nucleic acids. Some embodiments of detection of the bound target comprise plasmonic-particle labeled sample nucleic acids on a lower-density array, wherein the pitch may be in the range of a few microns to hundreds of microns or a few millimeters. The capture nucleic acids can be deposited on the pads in a pattern, such as a line, a plus sign, or any other symbol. The device can be illuminated from the back with an inexpensive light source, such as an LED or natural light. If the sample contains the target nucleic acids, the enhanced transmission mitigated by the presence of the plasmonic particles near the aperture will appear in the shape of the pattern, in this example a line or a plus sign, which can be read with an inexpensive detector placed proximally to the aperture array or at a distance determined by relay optics. Alternatively, the pattern could be detected by eye.

As discussed herein, the dielectric pillars 106 can have a circular cross-sectional shape. However, other shapes are also possible and can be used, in conjunction with the polarization of the pumping light, to perform higher resolution imaging.

Figure 9:
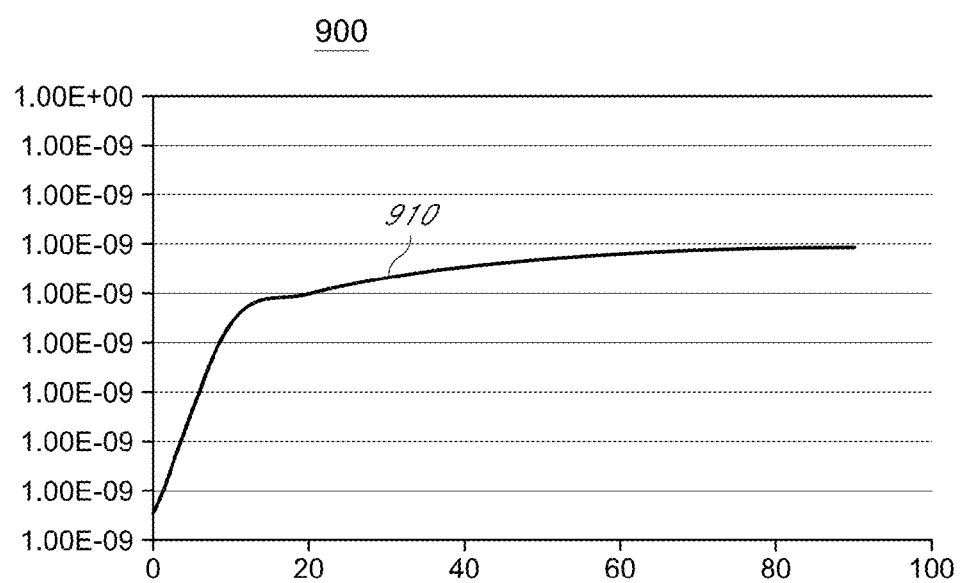
FIG. 9 is a graph that illustrates the sensitivity of non-rotationally symmetric dielectric pillars to shifts in the polarization of pumping light.

FIG. 9 is a graph 900 that illustrates the sensitivity of non-rotationally symmetric dielectric pillars 106 to shifts in the polarization of pumping light. The graph 900 is a plot of transmission of 700 nm light through dielectric pillars 106 having a rectangular cross-sectional shape as a function of polarization offset angle. Specifically, the cross sections of the dielectric pillars/apertures 106 are 100 nm×30 nm rectangles. These dielectric pillars 106 are apertures through a 300 nm layer 104 of gold. As illustrated in FIG. 9, there is a difference of approximately 5 orders of magnitude between the transmission of light through the dielectric pillars 106 when the polarization of the pumping light is aligned with the long side of the apertures versus when the polarization of the pumping light is aligned with the short side of the apertures. In particular, FIG. 9 shows that the transition occurs (for this particular example) when the polarization of the pumping light is misaligned from the orientation of the dielectric pillars 106 by about 10°. This polarization dependence of the transmission of light through the dielectric apertures 106 can be exploited to improve the spatial resolution of the analyte detection by the optical detector 120.

Figure 10:
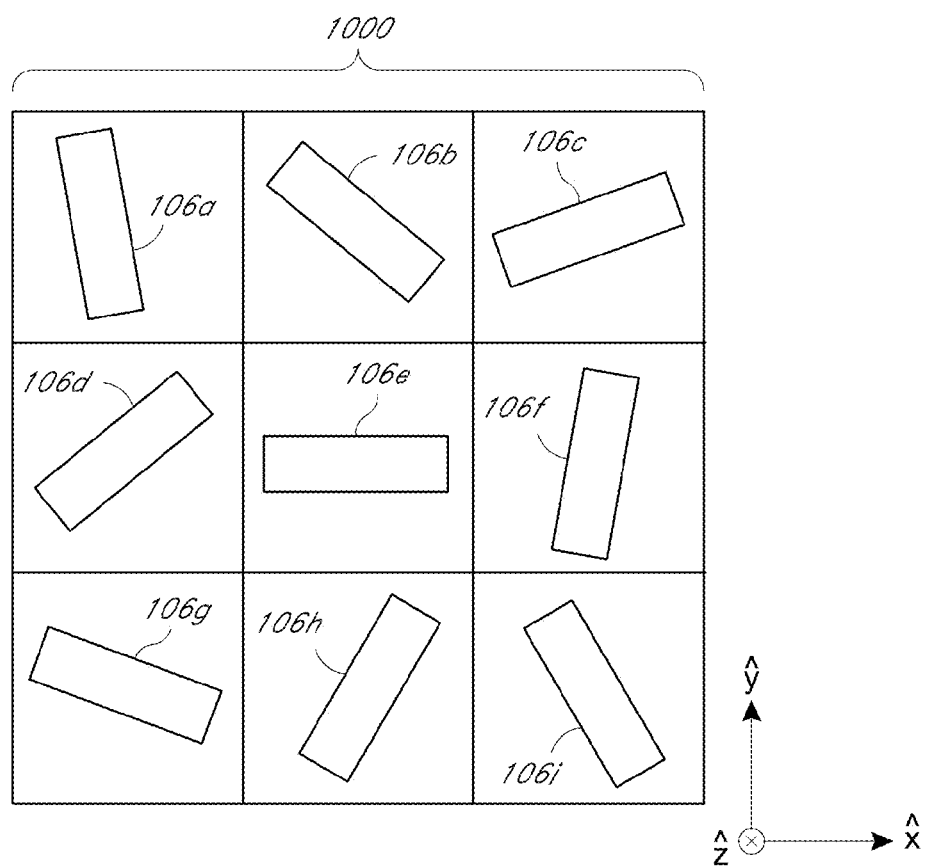
FIG. 10 illustrates a group of non-rotationally symmetric dielectric pillars arranged at different angular orientations so as to improve the spatial resolution of analyte detection.

FIG. 10 illustrates a group 1000 of non-rotationally symmetric dielectric pillars 106a-i arranged at different angular orientations so as to improve the spatial resolution of analyte detection. As illustrated in FIG. 10, each of the dielectric pillars 106 has a rectangular cross-section, though many other non-circular cross-sectional shapes are also possible and can likewise exhibit polarization dependence. Each of the rectangular dielectric pillars 106 in the group 1000 is arranged at a different angular orientation. Furthermore, each of the rectangular dielectric pillars 106 may be smaller than the diffraction limit of the optical detector 120. For example, the group 1000 as a whole can correspond to the approximate size of the smallest object that can be resolved in an image captured by the optical detector 120. Ordinarily, the optical detector 120 would, therefore, not be capable of resolving the precise spatial location of an analyte molecule or particle located at a specific one of the dielectric pillars 106a-i within the group 1000. However, by taking advantage of the polarization dependence of the dielectric pillars 106, sub-diffraction limit resolution is possible.

The location of an analyte molecule can be determined by pumping the dielectric pillars 106 using light having a first polarization angle. The optical detector 120 can be used to receive light from the optical sensor and create an image of the detection plane while pumping the dielectric pillars using light having the first polarization angle. The dielectric pillars 106 can then be pumped using light having a different second polarization angle. The optical detector 120 can be used to receive light from the optical sensor and create an image of the detection plane while pumping the dielectric pillars using light having the second polarization angle. Then a computer can be used to analyze the images of the detection plane to determine the location of the analyte molecule.

For example, the polarization of the pumping light from the light source 110 can be varied through a range of angular orientations in the XY plane. Images of the plane of the dielectric pillars 106 can be captured for a plurality of such polarizations. For example, if the polarization of the pumping light is set to 45°, then only dielectric pillars 106 whose angular orientation is 45° (plus or minus some misalignment tolerance in the polarization dependence) can be activated. (Conversely all of the dielectric pillars 106 except those whose angular orientation corresponds to the polarization of the pumping light can be activated.) In this way, based on the knowledge of the angular orientation of each dielectric pillar 106 and its precise spatial location, as well as knowledge of the polarization of the pumping light when each image is captured, the location of an analyte molecule or particle that is detected in a given image can be spatially resolved to a particular dielectric pillar 106 within the group 1000.

In a relatively simple case, the smallest diffraction-limited aperture size can be split into two rectangular apertures, each with an angular orientation offset by 90° from the other. This could result in a doubling of the spatial resolution of the system. However, as illustrated in FIG. 10, the smallest diffraction-limited apertures can also be split into N separate apertures (having N different angular orientations), in which case the spatial resolution of the system can be increased by a factor of N.

In addition to the foregoing polarization multiplexing technique for increasing the spatial resolution of the system, wavelength multiplexing can also be used. This is because the transmission of different wavelengths of light through the dielectric pillars 106 can also be dependent upon the aspect ratios of the apertures. For example, rectangular dielectric apertures 106 having different aspect ratios will exhibit their maximum difference between parallel and perpendicular polarizations at different wavelengths of the pumping light. Accordingly, by providing apertures of different aspect ratios, the wavelength of the pumping light can be varied across a range of wavelengths.

In some embodiments, the location of an analyte molecule can be determined by pumping the dielectric pillars 106 using light having a first wavelength. The optical detector 120 can be used to receive light from the optical sensor and create an image of the detection plane while pumping the dielectric pillars using light having the first wavelength. The dielectric pillars 106 can then be pumped using light having a different second wavelength. The optical detector 120 can be used to receive light from the optical sensor and create an image of the detection plane while pumping the dielectric pillars using light having the second wavelength. Then a computer can be used to analyze the images of the detection plane to determine the location of the analyte molecule.

For example, an image of the aperture plane can be collected for a plurality of different wavelengths of pumping light. For any given wavelength of pumping light, only those apertures having an aspect ratio that is excited by that wavelength of light are activated. (Conversely, all of the apertures except those of the particular aspect ratio can be activated.) In this way, based on the knowledge of the aspect ratio of each dielectric pillar 106 and its precise spatial location, as well as knowledge of the wavelength of the pumping light when each image is captured, the location of an analyte molecule or particle that is detected in a given image can be spatially resolved to a particular dielectric pillar 106 within the group 1000. This wavelength multiplexing technique for increasing spatial resolution can be used in conjunction with, or independent from, the polarization multiplexing technique.

FIGS. 11A-L illustrate an example method of fabrication for the optical sensor 100 illustrated in FIG. 1. In some embodiments, the method of fabrication begins with a wafer of bulk silicon in which pillars are formed. However, SOI wafers can also be used in some embodiments. The pillars can be formed using the processes discussed in U.S. Pat. No. 8,080,468, U.S. Patent Publication 2012/0118739, or U.S. Patent Publication 2012/0080361, which are hereby incorporated by reference in their entirety.

Lithography techniques, such as photolithography or electron beam lithography, can be used to pattern the pillars in the silicon. For example, in the case of electron beam lithography, a layer of electron beam resist can be provided on the surface of the silicon wafer. An electron beam can be used to expose the resist in such a way as to create a negative of the pattern of pillars that are to be formed. The resist layer can then be developed, leaving behind, for example, holes formed in the resist layer in the cross-sectional shape of the pillars. Next, a hard mask can be applied to the resist layer by sputtering on aluminum oxide using a reactive sputtering technique. The aluminum oxide fills the holes left behind after developing the resist. The resist is then lifted off with an organic solvent. This process also lifts off the aluminum oxide except in the locations of the pillars, where the aluminum oxide is layered directly on silicon rather than resist. Next, the silicon can be etched using plasma etching techniques. In some embodiments, the silicon is etched using a mixed-mode "pseudo-Bosch" technique to create the pillars in the silicon substrate.

Figure 11A:
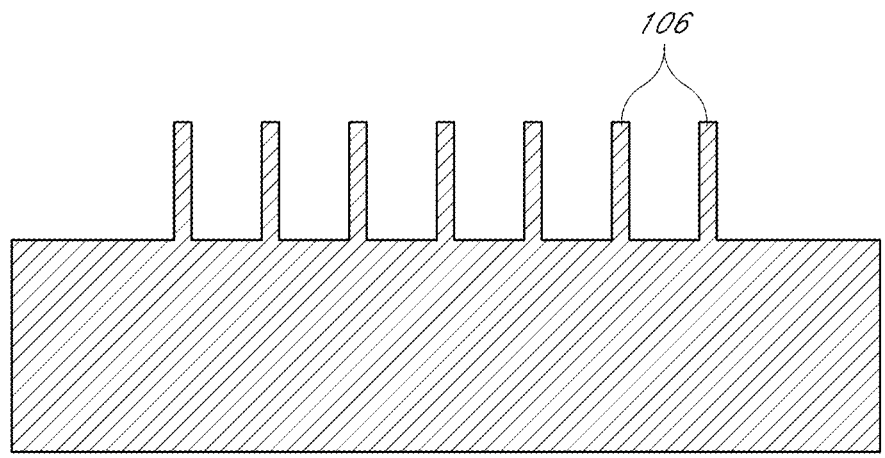
FIGS. 11A-L illustrate an example method of fabrication for the optical sensor illustrated in FIG. 1.

FIG. 11A illustrates the results of the etching process. As shown, pillars 106 are formed in the silicon substrate 102. Although the pillars are illustrated as having vertical sidewalls, the parameters of the etching process can be controlled so as to form any desired sidewall profile (e.g., tapered sidewalls).

Figure 11B:
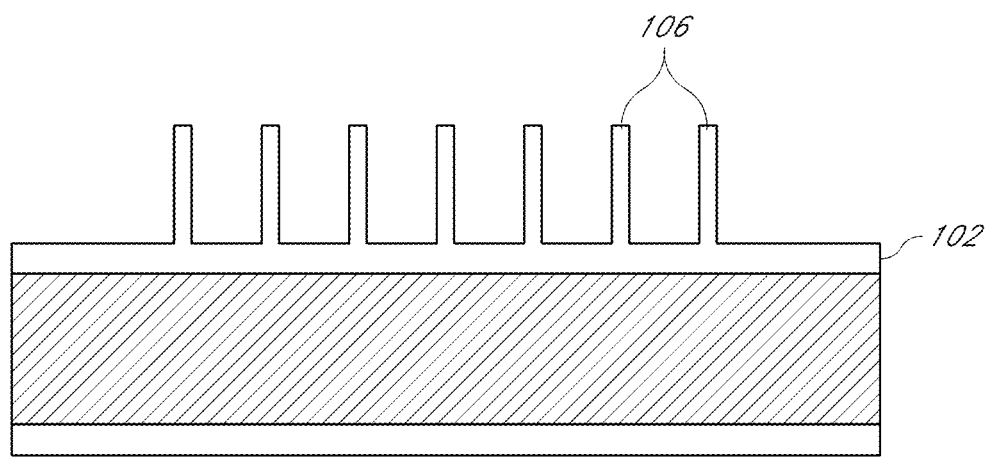

Next, in FIG. 11B, the silicon can be oxidized to convert the pillars 106 and a layer 102 of the silicon substrate into silicon dioxide. A dry oxidation ($O_2$-only ambient) process can be used. In some embodiments, the oxidation process is carried out for over three hours (eight hours may be typical) at a temperature of about 1000° C.

Figure 11C:
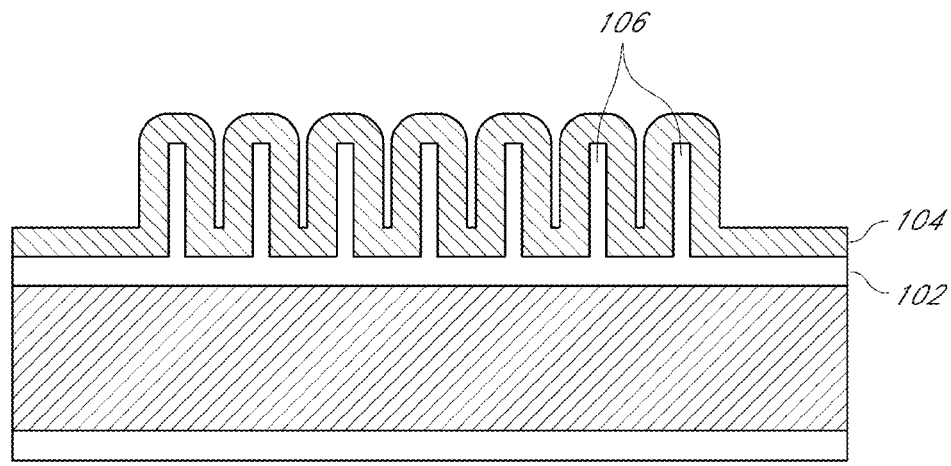

In FIG. 11C, a metallic layer 104 is applied to the dielectric pillars 106 and the dielectric layer 102. In some embodiments, first a relatively thin layer (e.g., about 4 nm) of titanium can be sputtered on. The layer of titanium can be followed by a relatively thicker layer of some other metal, such as gold. The titanium can help the gold to adhere to the silicon dioxide.

Figure 11D:
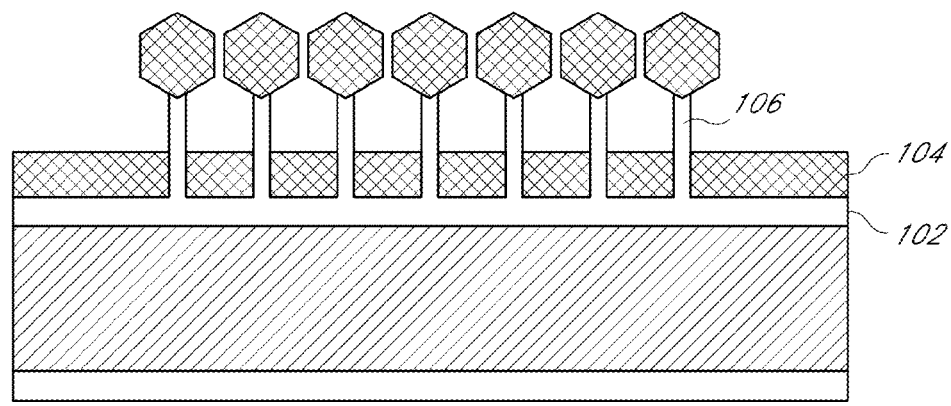

In FIG. 11D, the metallic layer 106 is heated, causing the metal to reflow. This reflow process removes metal from the sidewalls of the dielectric pillars 106, leaving behind a metallic layer 104 over the dielectric layer 102. The reflow process also causes metal to bead up on the tops of the dielectric pillars 106, as illustrated in FIG. 11D.

Figure 11E:
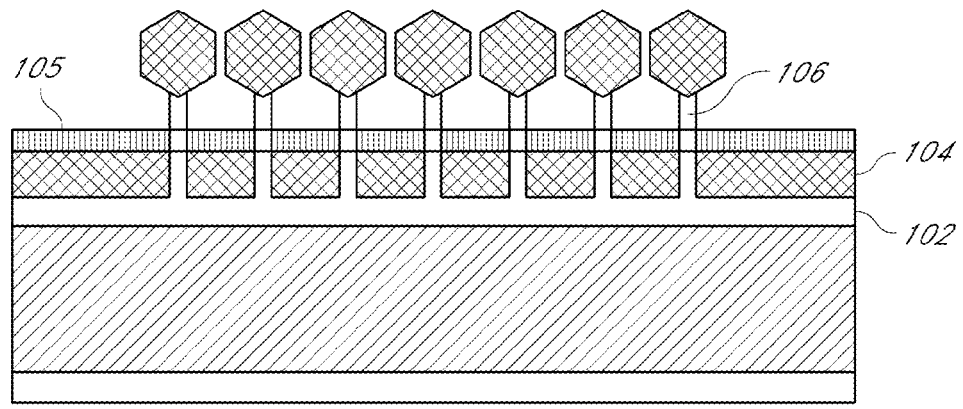

In FIG. 11E, a protective layer 105 is formed on the metallic layer 104. In some embodiments, the protective layer 105 can be poly(methyl methacrylate) (PMMA), which is spun on over the metallic layer 104. Other protective materials can also be used.

Figure 11F:
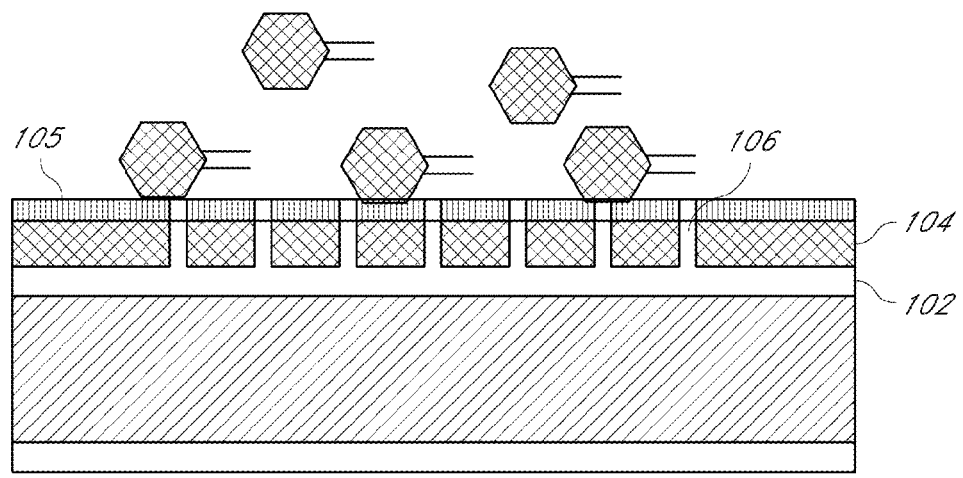
Figure 11G:
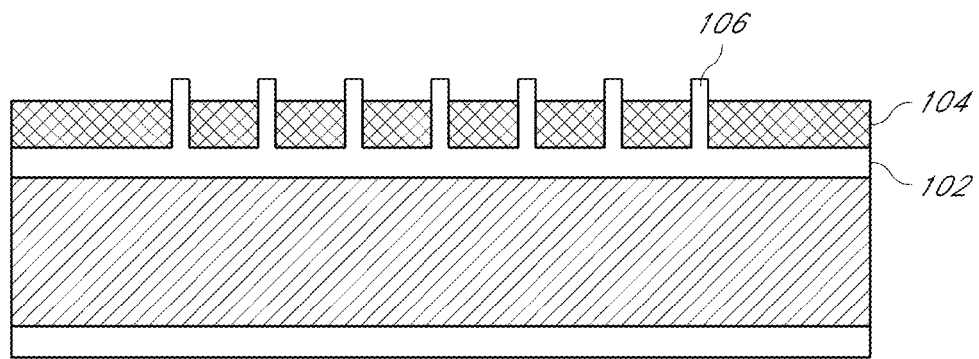
Figure 11H:
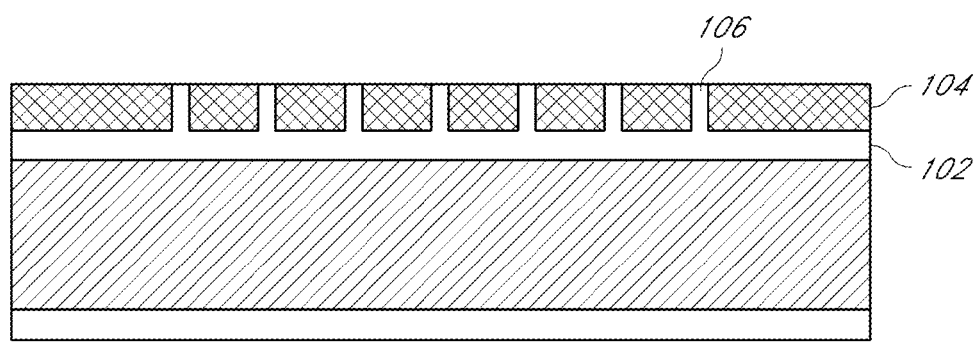

In FIG. 11F, the dielectric pillars 106 are snapped off, using applied mechanical force, flush with the level of the protective layer 105. In FIG. 11G, the protective layer 105 is dissolved away or otherwise removed. Next, in FIG. 11H, the protruding tips of the dielectric pillars 106 are etched flush with the top surface of the metallic layer 104.

Figure 11I:
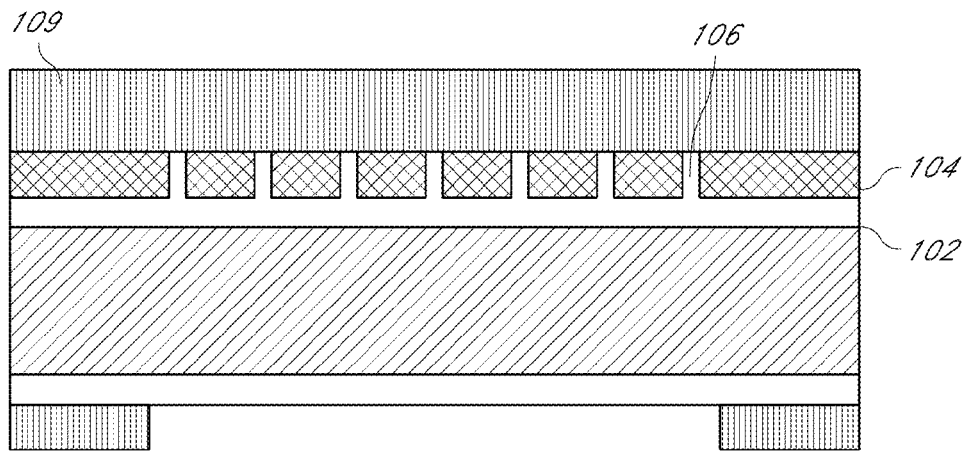
Figure 11J:
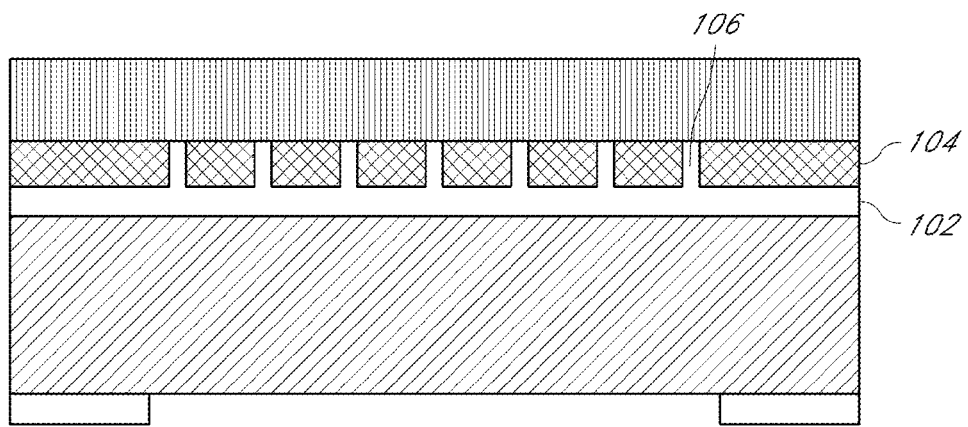

The window 108 can now be formed on the backside of the silicon substrate. In FIG. 11I, a protective layer 109 of PMMA is spun onto the top surface of the device. Resist can be applied to the backside of the substrate, and a window 108 can be patterned into the resist in the space beneath the array of dielectric pillars 106. In FIG. 11J, hydrofluoric acid can be used to remove the oxidation layer exposed by the window 108. In addition, the resist can be removed from the backside of the substrate. The result is a hard mask for window etching.

Figure 11K:
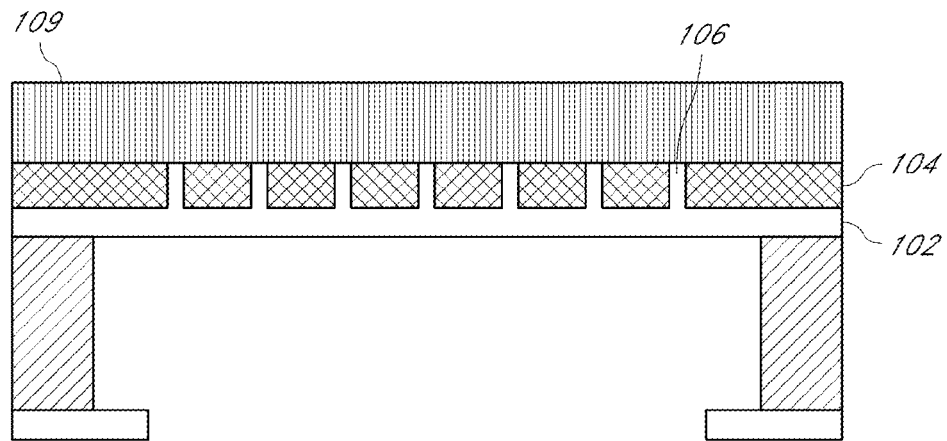
Figure 11L:
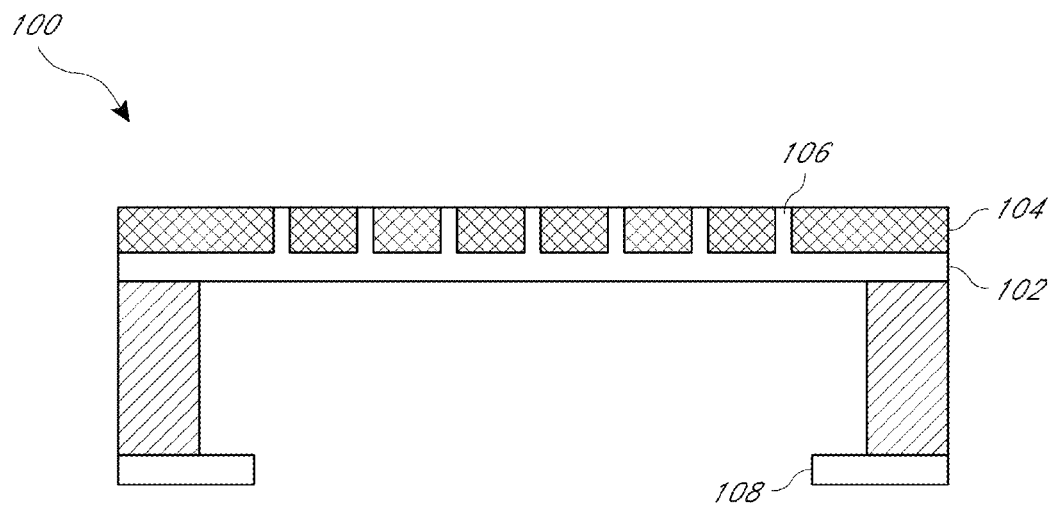

Next, in FIG. 11K, the bottom side of the silicon substrate is etched away, forming a window to the dielectric layer 102. In some embodiments, the dielectric layer 102 can likewise be etched away, exposing the metallic layer 104. Finally, in Figure the protective layer 109 of PMMA can be dissolved from the top surface of the device, resulting in the completed optical sensor 100.

Although FIGS. 11A-L illustrate an example method of fabrication for the optical sensor 100, other methods can also be used. Such methods may be known from, for example, the field of semiconductor manufacturing. In addition, other materials can also be used, as discussed herein.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps may be altered, added, removed, or rearranged. While certain embodiments have been explicitly described, other embodiments will become apparent to those of ordinary skill in the art based on this disclosure.

Any systems and methods described herein that involve computer processing can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers. In addition, where methods are described that are, or could be, at least in part carried out by computer software, it should be understood that such methods can be provided on computer-readable media (e.g., optical disks such as CDs or DVDs, hard disk drives, flash memories, diskettes, or the like) that, when read by a computer or other processing device, cause it to carry out the method.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. A device for detecting an analyte within a sample, the device comprising:
   a metallic layer; and
   a plurality of solid dielectric pillars extending through the metallic layer, the individual pillars having a uniform composition,
   wherein a plurality of regions of concentrated light are supported on one side of the device in proximity to the ends of the plurality of dielectric pillars when an opposite side of the device is illuminated and light propagates through the plurality of dielectric pillars.

2. The device of claim 1, further comprising a dielectric layer having a top surface and a bottom surface, wherein the metallic layer is formed on the top surface of the dielectric layer, and wherein the plurality of regions of concentrated light are supported in proximity to the ends of the plurality of dielectric pillars when the bottom surface of the metallic layer is illuminated.

3. The device of claim 2, further comprising a window formed on the bottom surface of the dielectric layer below the plurality of dielectric pillars.

4. The device of claim 1, wherein the plurality of regions of concentrated light comprise spatially-separated voxels above each of the plurality of dielectric pillars to which the light is substantially confined.

5. The device of claim 1, wherein the electric field strength of the light decays exponentially with height above the plurality of dielectric pillars.

6. The device of claim 1, wherein one or more of the plurality of dielectric pillars has a circular cross-section.

7. The device of claim 1, wherein one or more of the plurality of dielectric pillars has a non-rotationally symmetric cross-section.

8. The device of claim 7, wherein the plurality of dielectric pillars comprise a first pillar oriented with a first angular orientation, and a second pillar oriented with a different second angular orientation.

9. The device of claim 7, wherein the plurality of dielectric pillars comprise a first pillar with a first cross-sectional aspect ratio, and a second pillar with a second cross-sectional aspect ratio.

10. The device of claim 1, further comprising an optical detector configured to receive light from an object located in one of the regions of concentrated light, the analyte being capable of being detected based on the received light.

11. The device of claim 10, wherein the optical detector is capable of measuring detected light at a plurality of wavelengths.

12. The device of claim 1, wherein the dielectric pillars comprise silicon dioxide.

13. The device of claim 1, wherein metallic layer comprises gold.

14. The device of claim 1, wherein the plurality of dielectric pillars are functionalized such that the plurality of dielectric pillars are capable of specifically binding to an analyte of interest.

15. The device of claim 1, wherein one or more of the plurality of dielectric pillars are tapered.

16. The device of claim 15, wherein the narrowest portion of a tapered dielectric pillar is located on the side of the device nearest where a region of concentrated light is supported.

17. The device of claim 1, wherein the metallic layer has a thickness of between about 100 nm and about 500 nm.

18. The device of claim 1, wherein the plurality of dielectric pillars have a cross-sectional size of between about $\lambda/500$ and about $\lambda/2$, where $\lambda$ is the center wavelength of the light used to illuminate the device.

19. An analyte detection method comprising:
pumping an optical sensor with light, the optical sensor comprising a metallic layer, and a plurality of solid dielectric pillars extending through the metallic layer, the individual pillars having a uniform composition; and
receiving light from the optical sensor to detect an analyte of interest in a sample located in proximity to the optical sensor,
wherein pumping the optical sensor with light from one side of the optical sensor causes a plurality of regions of concentrated light to be supported on the other side of the optical sensor in proximity to the ends of the plurality of dielectric pillars when light propagates through the plurality of dielectric pillars.

20. The method of claim 19, wherein the light from the optical sensor to detect an analyte of interest comprises light from at least one of the regions of concentrated light.

21. The method of claim 19, wherein the light from the optical sensor to detect an analyte of interest comprises light emitted from a labeled analyte molecule located within at least one of the regions of concentrated light.

22. The method of claim 21, wherein the labeled analyte molecule is specifically bound to one of the dielectric pillars.

23. The method of claim 19, further comprising measuring detected light from the optical sensor at a plurality of wavelengths and detecting the analyte based on a change in the spectrum caused by the presence of the analyte within at least one of the regions of concentrated light.

* * * * *